United States Patent [19]
Aliev et al.

[11]  4,198,536
[45]  Apr. 15, 1980

[54] PROCESS FOR PREPARING BUTADIENE (DIVINYL)

[76] Inventors: Vagab S. Aliev, ulitsa Nizami, 66; Ramiz G. K. O. Rizaev, ulitsa Sharif-zade, 148, kv. 67; Veli S. M. O. Gadzhi-Kasumov, ulitsa Shirshova, 5, kv. 7; Beniamin G. Ter-Sarkisov, ulitsa 28 Aprelya, 14; Rashid M. Talyshinsky, ulitsa Vidadi, 160, kv. 16, all of Baku; Lidia P. Pilaeva, ulitsa Komsomolskaya, 3, kv. 23, Baku, poselok Razina; Zhalya M. K. Seifullaeva, ulitsa Chapaeva, 2a, kv. 5, Baku, all of U.S.S.R.

[21] Appl. No.: 973,756

[22] Filed: Dec. 28, 1978

[51] Int. Cl.$^2$ .................. C07C 5/48; C07C 11/16; B01J 23/18
[52] U.S. Cl. .................. 585/626; 208/134; 252/456; 252/464; 252/469; 585/658
[58] Field of Search .............. 260/680 E; 585/626; 252/456, 464, 469

[56]  References Cited
U.S. PATENT DOCUMENTS

| | | | |
|---|---|---|---|
| 3,577,477 | 5/1971 | Boutry et al. | 260/683.3 |
| 3,793,225 | 2/1974 | Bertus et al. | 252/437 |
| 3,801,671 | 4/1974 | Marsheck | 260/680 E |
| 4,039,583 | 8/1977 | Kawakami et al. | 260/680 E |

FOREIGN PATENT DOCUMENTS 1211332  1/1971 United Kingdom ............ 260/680 E

OTHER PUBLICATIONS

Chem. Abstracts 71, 80639u (1969) for Boutry et al., German Offen. 1,816,847, (equiv. to U. Kingdom 1,211,332).

Primary Examiner—Delbert E. Gantz
Assistant Examiner—G. E. Schmitkons
Attorney, Agent, or Firm—Lackenbach, Lilling & Siegel

[57] ABSTRACT

The process for preparing butadiene (divinyl) according to the present invention comprises dehydrogenation of n-butane or a mixture thereof with n-butene at a temperature ranging from 550° to 650° C. in the presence of oxygen, an inert diluent and a catalyst having the following composition, percent by weight:
  antimony oxide: 5.0–20.0
  vanadium oxide: 2.0–10.0
  nickel oxide: 4.0–20.0
  thorium oxide: 0.1–1.0
  titanium oxide: 0.1–1.0
  carrier: the balance.

The process of this invention makes it possible to increase simultaneously the yield and selectivity of the formation of divinyl.

6 Claims, No Drawings

PROCESS FOR PREPARING BUTADIENE (DIVINYL)

The present invention relates to the preparation of diolefin hydrocarbons and, more specifically, to a process for preparing butadiene, herein called divinyl.

Divinyl is one of the most important and large-scale produced monomers in the synthetic rubber industry. Recently divinyl has found extensive use in the synthesis of hexamethylenediamine and adipic acid.

Known in the art is a process for producing divinyl by oxidative dehydrogenation of n-butane in a stationary catalyst bed containing oxides of nickel, tin, phosphorus, potassium and sulphur at a temperature within the range of from 480° to 650° C., space velocity (as calculated for n-butane) of about 100 $hr^{-1}$, molar ratio between hydrocarbon, oxygen and steam equal to 1:(0.5–2):16. The yield of divinyl is equal to 10.9% by weight, selectivity for n-butenes is about 25% and maximal output of divinyl is about 10.9 l/l of the catalyst per hour. (Cf. U.S. Pat. No. 3,801,671).

Also known is a process for an oxidative dehydrogenation of n-butane on a catalyst consisting of oxides of molybdenum, cobalt and nickel. A mixture of n-butane with oxygen at the molar ratio therebetween of 1:0.5 is passed through a stationary bed of the catalyst. Conversion of n-butane is about 20%, selectivity for n-butenes—about 26%, for divinyl—about 35%; maximum output of divinyl amounts to about 50.4 l/l of the catalyst per hour (cf. British Pat. No. 1,211,332 and its equivalent U.S. Pat. No. 3,577,477).

Another known process for an oxidative dehydrogenation of n-butane is effected in a stationary bed of catalyst composed of cobalt and magnesium oxides at a temperature of 550° C., space velocity of n-butane of 300 $hr^{-1}$ and a molar ratio between hydrocarbon, oxygen and steam of 1:0.5:10. Conversion of n-butane is about 28%, selectivity for divinyl—about 43%, output of divinyl—about 36 l/l of the catalyst per hour (cf. USSR Inventor's Certificate No. 440150).

Still another known process for an oxidative dehydrogenation of n-butane is effected in a stationary bed of nickel molybdate at a temperature within the range of from 550° to 590° C., space velocity of the hydrocarbon supply of 50 to 500 $hr^{-1}$ and at the molar ratio between n-butane, oxygen and steam of 1:1:20. The yield of divinyl is 4.2–13.5% by weight, selectivity for divinyl—about 33%, output of divinyl is equal to 67.5 l/l of the catalyst per hour (Cf. U.S. Pat. No. 3,793,225).

Known in the art is also a process for preparing divinyl by oxidative hydrogenation of n-butane or a mixture thereof with n-butene in a stationary bed of an oxide catalyst containing Sb, Bi, V, Mo and deposited onto γ—$Al_2O_3$ at a temperature within the range of from 550° to 650° C., space velocity for n-butane of from 500 to 750 $hr^{-1}$ and molar ratio between the hydrocarbon, oxygen and steam equal to 1:(0.7–1):(15–25). The yield of divinyl as calculated for the passed n-butane upon dehydrogenation of n-butane or butane-butene mixtures is 14 to 18 mol.% selectivity for divinyl 50–66.5%. Maximum output of divinyl is equal to 126.0 l/l of the catalyst per hour (Inventor's Certificate No. 551856).

These prior art processes have disadvantages residing in low yield and selectivity in the formation of divinyl and lack of an optimal combination of these two factors, i.e. maximum yield of divinyl is always associated with an insufficient selectivity, while a high selectivity of the process is associated with a relatively low yield of divinyl, whereby an insufficient output of divinyl per unit volume of catalyst is obtained.

It is an object of the present invention to increase the yield of divinyl and improve the process selectivity.

This object is accomplished by a process for preparing divinyl which comprises dehydrogenation of n-butane or a mixture thereof with n-butene at a temperature within the range of from 550° to 650° C. in the presence of oxygen, an inert diluent and a catalyst of the following composition, percent by weight:

antimony oxide: 5.0 to 20.0
vanadium oxide: 2.0 to 10.0
nickel oxide: 4.0 to 20.0
thorium oxide: 0.1 to 1.0
titanium oxide: 0.1 to 1.0
carrier: the balance.

The above-mentioned catalyst composition makes it possible to considerably increase the yield of divinyl and the process selectivity simultaneously with an increased output of the product per unit volume of the catalyst.

It is advisable, with the view to increase the yield and selectivity of the formation of divinyl, to use the catalyst having the following composition, percent by weight:

antimony oxide: 7.0 to 15.0
vanadium oxide: 4.0 to 8.0
nickel oxide: 7.0 to 13.0
thorium oxide: 0.4 to 0.6
titanium oxide: 0.4 to 0.6
carrier: the balance.

It is advisable to use a catalyst containing alumina as the carrier and conduct the process at a molar ratio between the hydrocarbon, oxygen and an inert diluent equal to 1:(0.25–2.0):(4–40). It is preferable to use steam, nitrogen or carbon dioxide as the inert diluent and conduct the process at a space velocity of the hydrocarbon supply of from 100 to 750 $hr^{-1}$.

The process for preparing divinyl according to the present invention is performed in the following manner.

The hydrocarbon feed, oxygen and an inert diluent are passed through a reactor with a stationary bed of catalyst at a temperature within the range of from 550° to 650° C. at a molar ratio between the hydrocarbon, oxygen and the inert diluent of 1:(0.25–2.0):(4–40) at a space velocity of the hydrocarbon feed supply of from 100 to 750 $hr^{-1}$. As the hydrocarbon feed, use is made of n-butane or various mixtures of n-butane and n-butenes corresponding to the coefficient of process stage number of about 1 under the predetermined conditions of the experiments, while as the inert diluent, use is made of steam, nitrogen or carbon dioxide. Recovery of divinyl from the contact gas after separation of the water condensate and drying is effected either by the desorption method, azeotropic or extractive distillation or by chemisorption method. The unreacted n-butane and n-butenes may be recycled back to the reaction system.

It is also possible to perform the process in a sectioned reactor with a stationary bed of the catalyst. Supply of oxygen and temperature control are effected independently for each section. This makes it possible to carry out the process under adiabatic conditions, maintain a substantially permanent concentration of oxygen, close to the optimal one, in the reaction zone and considerably simplify the process equipment for commercial implementation.

In the process according to the present invention, use is made of a catalyst having the following composition, percent by weight:
antimony oxide: 5.0 to 20.0
vanadium oxide: 2.0 to 10.0
nickel oxide: 4.0 to 20.0
thorium oxide: 0.1 to 1.0
titanium oxide: 0.1 to 1.0
carrier: the balance.

The catalyst is prepared in the following manner: to a solution of nickel nitrate there are added appropriate amounts of solutions of antimony, vanadium, thorium and titanium salts, whereafter the solution temperature is brought to 40°–50° C. and a carrier, i.e. $Al_2O_3$ preliminarily calcined at a temperature within the range of from 700° to 900° C. for 24 hours is added thereto. The solution is maintained at said temperature of 40° to 50° C. for a period of 5 to 6 hours and then evaporated.

The remaining mass is dried at a temperature within the range of from 120° to 140° C. over a period of from 2 to 4 hours then calcined in a current of air at a temperature of from 550° to 650° C. for 6 to 8 hours. As a result, a catalyst is obtained consisting of a mixture of oxides of antimony, vanadium, nickel, titanium and thorium deposited on a carrier. Prior to operation, the catalyst is activated by passing alternate streams of oxygen, hydrocarbon feed and steam for 6 hours, while gradually elevating the temperature from 550° to 650° C.

The process for the preparation of divinyl according to the present invention has certain advantages over the prior art processes which reside in a considerable simultaneous increase of the yield and selectivity of divinyl formation as well as simplicity of industrial implementation of the process. The amount of by-products is considerably decreased due to an increased selectivity of the catalyst. The catalyst is characterized by a high output of divinyl, stability of operation, mechanical strength and it does not require periodic regeneration.

For a better understanding of the process according to the present invention, some specific Examples are given hereinbelow by way of illustration.

EXAMPLE 1

Through a sectioned reactor with a stationary bed of catalyst, a mixture of a hydrocarbon feed, oxygen and steam taken in the molar ratio of 1:1.4:40 respectively, is passed at a space velocity of the hydrocarbon feed supply of 100 hr$^{-1}$. The hydrocarbon feed has the following composition, mol.%: n-butane 85; n-butenes 15. Supply of oxygen and temperature control are effected separately in each section. The molar ratio between oxygen and the hydrocarbon feed in the reactor sections is the following:
section I: 0.5
section II: 0.5
section III: 0.4
Temperature in the reactor sections is equal to, °C.:
section I: 600
section II: 620
section III: 615
The catalyst has the following composition, percent by weight:
antimony oxide: 15.0
vanadium oxide: 7.0
nickel oxide: 4.0
thorium oxide: 0.5
titanium oxide: 0.1
aluminum oxide: the balance.
Conversion of n-butane is 28.4%.
Selectivity as calculated for divinyl is 50%.
Output of divinyl is 14.2 l/l of the catalyst per hour.

EXAMPLE 2

The process is effected in a manner similar to that described in the foregoing Example 1, except that the molar ratio between the hydrocarbon feed, oxygen and steam is equal to 1:1.2:36 respectively. The molar ratio between oxygen and the hydrocarbon feed in the reactor sections is the following:
section I: 0.5
section II: 0.4
section II: 0.3.
Temperature in the reactor sections is the following, °C.:
section I: 620
section II: 650
section III: 620
The catalyst has the following composition, percent by weight:
antimony oxide: 5.0
vanadium oxide: 2.0
nickel oxide: 12.0
thorium oxide: 1.0
titanium oxide: 1.0
aluminum oxide: the balance.
Conversion of n-butane is equal to 34.0%.
Selectivity with respect to divinyl is 40.1%.
Output of divinyl is 13.6 l/l of the catalyst per hour.

EXAMPLE 3

The procedure of Example 1 hereinbefore is repeated, except that the molar ratio between the hydrocarbon feed, oxygen, and steam is equal to 1:1.0:30 respectively and the space rate of the hydrocarbon feed supply is equal to 200 hr$^{-1}$.
Molar ratio in the reactor sections is the following:
section I: 0.4
section II: 0.3
section III: 0.3
Temperature in the reactor sections is the following, °C.:
section I: 620
section II: 630
section III: 630
The catalyst has the following composition, percent by weight:
antimony oxide: 7.5
vanadium oxide: 3.5
nickel oxide: 6.0
thorium oxide: 0.1
titanium oxide: 0.5
aluminum oxide: the balance
Conversion of n-butane is equal to 34.8%.
Selectivity with respect to divinyl is equal to 38.5%.
Output of divinyl is 26.8 l/l of the catalyst per hour.

EXAMPLE 4

Through a sectioned reactor with a stationary bed of catalyst, a mixture of a hydrocarbon feed, oxygen and steam taken in a molar ratio of 1:1.25:33 respectively is passed at a space velocity of the hydrocarbon feed supply of 300 hr$^{-1}$. The hydrocarbon feed has the following composition, molar percent: n-butane 86.5, n-butenes 13.5.

The supply of oxygen and control temperature are performed independently in each section. The molar ratio between oxygen and the hydrocarbon feed in the reactor sections is the following:
section I: 0.52
section II: 0.38
section III: 0.35.
Temperature in the reactor sections is the following, °C.:
section I: 615
section II: 628
section III: 630.
The catalyst has the following composition, percent by weight:
antimony oxide: 11.0
vanadium oxide: 4.5
nickel oxide: 9.0
thorium oxide: 0.5
titanium oxide: 0.5
aluminum oxide: the balance.
Conversion of n-butane is equal to 45.8%.
Selectivity with respect to divinyl is equal to 57.7%.
Output of divinyl is 79.3 l/l of the catalyst per hour.

EXAMPLE 5

The procedure of the foregoing Example 4 is repeated. The catalyst has the following composition, percent by weight:
antimony oxide: 11.0
vanadium oxide: 9.0
nickel oxide: 4.5
thorium oxide: 0.5
titanium oxide: 0.5
aluminum oxide: the balance.
Conversion of n-butane is equal to 42.0%.
Selectivity with respect to divinyl is 50.0%.
Output of divinyl is 63.0 l/l of the catalyst per hour.

EXAMPLE 6

Through a sectioned reactor with a stationary bed of catalyst a mixture of a hydrocarbon, oxygen and steam in a molar ratio of 1:1.2:28 respectively is passed at a space velocity of the hydrocarbon feed supply of 300 hr$^{-1}$. The hydrocarbon feed has the following composition, mol.%: n-butane 86.5, n-butenes 13.5.
Supply of oxygen and temperature control are effected independently in each section of the reactor. The molar ratio in the reactor sections is the following:
section I: 0.50
section II: 0.40
section III: 0.30
Temperature in the reactor sections is the following, °C.:
section I: 610
section II: 620
section III: 625
The catalyst has the following composition, percent by weight:
antimony oxide: 11.0
vanadium oxide: 4.5
nickel oxide: 9.0
thorium oxide: 0.5
titanium oxide: 0.5
aluminum oxide: the balance.
Conversion of n-butane is equal to 38.3%.
Selectivity with respect to divinyl is equal to 59.0%.
Output of divinyl is 67.8 l/l of the catalyst per hour.

EXAMPLE 7

The procedure of the foregoing Example 6 is repeated, except that the molar ratio between the hydrocarbon feed, oxygen and steam is equal to 1:1.2:25 respectively. The molar ratio between oxygen and the hydrocarbon feed (n-butane 86.5 mol.%, n-butenes 13.5 mol.%) in the reactor sections is the following:
section I: 0.48
section II: 0.38
section III: 0.33
The catalyst has the composition similar to that described in the foregoing Example 6.
Conversion of n-butane is equal to 39.6%.
Selectivity with respect to divinyl is 55.9%.
Output of divinyl is 66.3 l/l of the catalyst per hour.

EXAMPLE 8

The procedure of the foregoing Example 6 is repeated, except that the molar ratio between the hydrocarbon feed, oxygen and steam is equal to 1:1.05:20 respectively. The hydrocarbon feed has the following composition, mol.%: n-butane 92.0, n-butenes 8.0. The molar ratio between oxygen and the hydrocarbon feed in the reactor sections is the following:
section I: 0.50
section II: 0.30
section III: 0.25
Temperature in the reactor sections is the following, °C.:
section I: 620
section II: 610
section III: 610
The catalyst has the following composition, percent by weight:
antimony oxide: 11.0
vanadium oxide: 4.5
nickel oxide: 9.0
thorium oxide: 0.5
titanium oxide: 0.5
aluminum oxide: the balance.
Conversion of n-butane is 34.9%.
Selectivity with respect to divinyl is equal to 46.5%.
Output of divinyl is 48.7 l/l of the catalyst per hour.

EXAMPLE 9

Through a sectioned reactor with a stationary bed of catalyst, a mixture of n-butane, oxygen and carbon dioxide is passed at a molar ratio between the components of 1:1.1:12 respectively and at the space rate of n-butane supply of 450 hr$^{-1}$. Oxygen supply and temperature control are effected independently in each section of the reactor. The molar ratio between oxygen and n-butane in the reactor sections is the following:
section I: 0.5
section II: 0.3
section III: 0.3
Temperature in the reactor sections is the following, °C.:
section I: 620
section II: 620
section III: 640
The catalyst has the following composition, percent by weight:
antimony oxide: 20.0
vanadium oxide: 2.0
nickel oxide: 6.5
thorium oxide: 0.3 titanium oxide: 0.2
aluminum oxide: the balance.
Conversion of n-butane is equal to 30.6%.
Selectivity with respect to divinyl is 40.3%.
Output of divinyl is 55.4 l/l of the catalyst per hour.

EXAMPLE 10

Through a sectioned reactor with a stationary bed of a catalyst, a mixture of n-butane, oxygen and nitrogen is passed at the molar ratio of the components of 1:0.8:25 respectively and at a space velocity of n-butane supply of 150 hr$^{-1}$. Oxygen supply and temperature control are effected independently in each section of the reactor. The molar ratio between oxygen and n-butane in the reactor sections is the following:
  section I: 0.3
  section II: 0.2
  section III: 0.3
Temperature in the reactor sections is the following, °C.:
  section I: 630
  section II: 630
  section III: 640
The catalyst has the following composition, percent by weight:
  antimony oxide: 5.0
  vanadium oxide: 10.0
  nickel oxide: 20.0
  thorium oxide: 0.8
  titanium oxide: 0.6
  aluminum oxide: the balance.
Conversion of n-butane is equal to 41.5%.
Selectivity with respect to divinyl is 32.8%.
Output of divinyl is 20.4 l/l of the catalyst per hour.

EXAMPLE 11

Through a reactor with stationary bed of a catalyst a mixture of n-butane, oxygen and steam is passed at the temperature of 600° C., space rate of n-butane supply of 750 hr$^{-1}$ and at the molar ratio between the components of 1:0.5:7 respectively. The catalyst has the following composition; percent by weight:
  antimony oxide: 13.0
  vanadium oxide: 8.5
  nickel oxide: 10.5
  thorium oxide: 0.9
  titanium oxide: 0.3
  aluminum oxide: the balance.
Conversion of n-butane is equal to 18.3%.
Selectivity with respect to divinyl is equal to 24.2%.
Selectivity with respect to n-butenes is equal to 19.8%.
Output of divinyl is 33.0 l/l of the catalyst per hour.

EXAMPLE 12

Through a reactor with stationary bed of a catalyst a mixture of a hydrocarbon feed, oxygen and steam in a molar ratio of 1:0.25:4 respectively is passed at a temperature of 620° C. and at the space rate of the hydrocarbon feed supply of 400 hr$^{-1}$. The hydrocarbon feed has the following composition, molar percent: n-butane 90.0, n-butenes 10.0.
The catalyst has the following composition, percent by weight:
  antimony oxide: 10.0
  vanadium oxide: 5.0
  nickel oxide: 14.0
  thorium oxide: 0.8
  titanium oxide: 0.2
  aluminum oxide: the balance.
Conversion of n-butane is 22.8%.
Selectivity with respect to divinyl is 28.3%.
Output of divinyl is 25.8 l/l of the catalyst per hour.

EXAMPLE 13

Through a reactor with a stationary bed of a catalyst a mixture of n-butane, oxygen and steam at the molar ratio therebetween of 1:0.4:4 respectively is passed at a temperature of 630° C. and space velocity of n-butane supply of 750 hr$^{-1}$. The catalyst has the following composition, percent by weight:
  antimony oxide: 11.0
  vanadium oxide: 4.5
  nickel oxide: 9.0
  thorium oxide: 0.5
  titanium oxide: 0.5
  aluminum oxide: the balance.
Conversion of n-butane is equal to 25.0%.
Selectivity with respect to divinyl is equal to 60%.
Selectivity with respect to n-butenes is equal to 29.4%.
Output of divinyl is 112.5 l/l of the catalyst per hour.

EXAMPLE 14

Through a reactor with a stationary bed of catalyst a mixture of n-butane, oxygen and steam at a molar ratio therebetween of 1:0.8:8 respectively is passed at a temperature of 620° C. and space velocity of n-butane supply of 600 hr$^{-1}$.
The catalyst has the following composition, percent by weight:
  antimony oxide: 12.0
  vanadium oxide: 4.5
  nickel oxide: 7.0
  thorium oxide: 0.7
  titanium oxide: 0.5
  aluminum oxide: the balance.
Conversion of n-butane is equal to 21.0%.
Selectivity with respect to divinyl is equal to 49.1%.
Selectivity with respect to n-butenes is equal to 21%.
Output of divinyl is 61.9 l/l of the catalyst per hour.

EXAMPLE 15

Through a reactor with a stationary bed of catalyst a mixture of a hydrocarbon feed, oxygen and steam at a molar ratio therebetween of 1:2:30.0 respectively is passed at a temperature of 625° C. and space velocity of the hydrocarbon feed supply of 100 hr$^{-1}$. The hydrocarbon feed contains, mol.%: n-butane 95.0, n-butenes 5.0.
The catalyst has the following composition, percent by weight:
  antimony oxide: 20.0
  vanadium oxide: 2.0
  nickel oxide: 4.0
  thorium oxide: 0.1
  titanium oxide: 0.1
  aluminum oxide: the balance.
Conversion of n-butane is equal to 16.5%.
Selectivity with respect to divinyl is 10.5%.
Output of divinyl is 1.73 l/l of the catalyst per hour.

EXAMPLE 16

Through a reactor with a stationary bed of catalyst a mixture of n-butane, oxygen and steam at a molar ratio therebetween of 1:2:30 respectively is passed at a temperature of 600° C. and space velocity of n-butane supply of 100 hr$^{-1}$. The catalyst has the following composition, percent by weight:
- antimony oxide: 5.0
- vanadium oxide: 10.0
- nickel oxide: 20.0
- thorium oxide: 1.0
- titanium oxide: 0.1
- aluminum oxide: the balance.

Conversion of n-butane is equal to 13.2%.
Selectivity with respect to divinyl is 7.5%.
Output of divinyl is 1.0 l/l of the catalyst per hour.

EXAMPLE 17

Through a reactor with a stationary bed of catalyst a mixture of a hydrocarbon feed, oxygen and steam at a molar ratio therebetween of 1:0.6:7 respectively is passed at a temperature of 630° C. and space velocity of the hydrocarbon feed supply of 750 hr$^{-1}$. The hydrocarbon feed contains: 90.0 mol.% of n-butane and 10.0 mol.% of n-butenes.

The catalyst has the following composition, percent by weight:
- antimony oxide: 12.5
- vanadium oxide: 5.0
- nickel oxide: 10.0
- thorium oxide: 0.4
- titanium oxide: 0.5
- aluminum oxide: the balance.

Conversion of n-butane is equal to 28.7%.
Selectivity relative to divinyl is 71.9%.
Output of divinyl is 154.5 l/l of the catalyst per hour.

EXAMPLE 18

Through a reactor with a stationary bed of catalyst, a mixture of a hydrocarbon feed, oxygen and steam is passed at a molar ratio between the components of 1:1.5:20 respectively, temperature of 640° C. and at a space velocity of the hydrocarbon feed supply of 250 hr$^{-1}$. The hydrocarbon feed contains: 90.0 mol.% of n-butane and 10.0 mol.% of n-butene.

The catalyst has the following composition, percent by weight:
- antimony oxide: 15.0
- vanadium oxide: 8.0
- nickel oxide: 5.0
- thorium oxide: 0.5
- titanium oxide: 0.3
- aluminum oxide: the balance.

Conversion of n butane is 31.8%.
Selectivity relative to divinyl is 23.9%.
Output of divinyl is 19.0 l/l of the catalyst per hour.

EXAMPLE 19

Through a reactor with a stationary bed of catalyst, a mixture of n-butane, oxygen and nitrogen at a molar ratio of 1:0.8:6 respectively is passed at a temperature of 635° C. and space velocity of n-butane supply of 650 hr$^{-1}$.

The catalyst has the following composition, percent by weight:
- antimony oxide: 12.5
- vanadium oxide: 6.0
- nickel oxide: 9.5
- thorium oxide: 0.4
- titanium oxide: 0.5
- aluminum oxide: the balance.

Conversion of n-butane is equal to 25.6%.
Selectivity with respect to divinyl is 56.2%.
Selectivity with respect to n-butenes is 28.4%.
Output of divinyl is 93.6 l/l of the catalyst per hour.

EXAMPLE 20

Through a reactor with a stationary bed of catalyst, a mixture of n-butane, oxygen and carbon dioxide at a molar ratio therebetween of 1:1.5:16 respectively is passed at a temperature of 600° C. and space velocity of n-butane supply of 200 hr$^{-1}$. The catalyst has the following composition, percent by weight: antimony oxide 15.0
- vanadium oxide: 8.5
- nickel oxide: 10.0
- thorium oxide: 1.0
- titanium oxide: 0.1
- aluminum oxide: the balance.

Conversion of n-butane is 21.4%.
Selectivity with respect to divinyl is equal to 40.0%.
Selectivity with respect to n-butenes is equal to 22.7%.
Output of divinyl is 17.12 l/l of the catalyst per hour.

What is claimed is:

1. A process for preparing divinyl comprising dehydrogenation of n-butane or a mixture thereof with n-butenes at a temperature ranging from 550° to 650° C. in the presence of oxygen, an inert diluent and a catalyst of the following composition, percent by weight:
- antimony oxide: 5.0–20.0
- vanadium oxide: 2.0–10.0
- nickel oxide: 4.0–20.0
- thorium oxide: 0.1–1.0
- titanium oxide: 0.1–1.0
- carrier: the balance.

2. A process as claimed in claim 1, wherein the catalyst has the following composition, percent by weight:
- antimony oxide: 7.0–15.0
- vanadium oxide: 4.0–8.0
- nickel oxide: 7.0–13.0
- thorium oxide: 0.4–0.6
- titanium oxide: 0.4–0.6
- carrier: the balance.

3. A process as claimed in claim 1, wherein a catalyst is used which contains alumina as a carrier.

4. A process as claimed in claim 1, wherein the molar ratio between the hydrocarbon, oxygen and the inert diluent is equal to 1:(0.25–2.0):(4–40).

5. A process as claimed in claim 1, wherein the inert diluent is selected from the group consisting of steam, nitrogen and carbon dioxide.

6. A process as claimed in claim 1, wherein the space velocity of the hydrocarbon supply is varied from 100 to 750 hr$^{-1}$.

* * * * *